United States Patent [19]
Perry et al.

[11] Patent Number: 5,817,517
[45] Date of Patent: Oct. 6, 1998

[54] METHOD OF CHARACTERIZING FEEDS TO CATALYTIC CRACKING PROCESS UNITS

[75] Inventors: Bruce N. Perry; James Milton Brown, both of Flemington, N.J.

[73] Assignee: Exxon Research and Engineering Company, Florham Park, N.J.

[21] Appl. No.: 918,540

[22] Filed: Aug. 22, 1997

Related U.S. Application Data

[63] Continuation of Ser. No. 731,040, Oct. 8, 1996, abandoned, which is a continuation of Ser. No. 385,257, Feb. 8, 1995, abandoned.

[51] Int. Cl.[6] .......................... G01N 33/22; G01N 33/26
[52] U.S. Cl. ............................... 436/55; 436/52; 436/60; 436/139; 436/140; 436/141; 436/142; 436/164; 250/339.12; 250/343
[58] Field of Search ............................. 250/339.12, 343; 436/52, 55, 60, 139, 140, 141, 142, 164

[56] References Cited

U.S. PATENT DOCUMENTS

| | | | |
|---|---|---|---|
| 4,282,084 | 8/1981 | Gross et al. | 208/113 |
| 4,963,745 | 10/1990 | Maggard | 250/343 |
| 5,082,985 | 1/1992 | Crouzet et al. | |
| 5,121,337 | 6/1992 | Brown | 364/498 |
| 5,145,785 | 9/1992 | Maggard et al. | 436/8 |
| 5,223,714 | 6/1993 | Maggard et al. | 250/343 |
| 5,225,679 | 7/1993 | Clark et al. | 250/343 |
| 5,348,645 | 9/1994 | Maggard et al. | 208/209 |
| 5,349,189 | 9/1994 | Maggard | 250/339.07 |
| 5,360,972 | 11/1994 | Di Foggio et al. | 250/339.12 |
| 5,407,830 | 4/1995 | Altman et al. | 436/55 |
| 5,412,581 | 5/1995 | Tackett | 364/498 |

FOREIGN PATENT DOCUMENTS

| | | |
|---|---|---|
| 304232 | 2/1989 | European Pat. Off. . |
| 2217838 | 11/1989 | United Kingdom . |
| 9408226 | 4/1994 | WIPO . |

OTHER PUBLICATIONS

V.C. Utterback *Chem. Eng.* 1976, 83, 141–144.
R.C. Fox *Anal. Chem.* 1976, 48, 717–721.
P.G. Coxson et al. *Ind. Eng. Chem. Res.* 1987, 26, 1239–1248.
L.C. Yen et al. *Oil Gas J.* 1988, 86, 67–70.
M.Y. Chou et al *AICHE J.* 1988, 34, 1519–1527.
L.L. Oliveira et al. *Ind. Eng. Chem. Res.* 1989, 28, 264–271.
J.J. Kelly et al. *Anal. Chem.* 1990, 62, –1444–1451.
L.U. Gron et al. *Prep. Pap. ACS Div. Petrol. Chem.* 1992, 37, 793–797.
G.E. Fodor et al. *Energy Fuel* 1993, 7, 598–601.
W.T. Welch et al.*Oil Gas J.* 1994, 92, 48& 51–56.
W.J. Fateley et al. CPAC Informational Document Announcement #53, 1994.
J. Ren et. al. *Che,. Abstr.* 1995, 122, 269618z.

*Primary Examiner*—Arlen Soderquist
*Attorney, Agent, or Firm*—Ronald D. Hantman

[57] ABSTRACT

The present invention is a method to determine the chemical concentration of one or more of a number of the constituent classes of a feed to a catalytic cracking process. These constituent classes which are referred to as "lumps", include 14 different molecular types in 4 different boiling range fractions. A specific lump will include all individual molecular components which are expected to react in a similar way in the catalytic cracking unit.

11 Claims, 18 Drawing Sheets

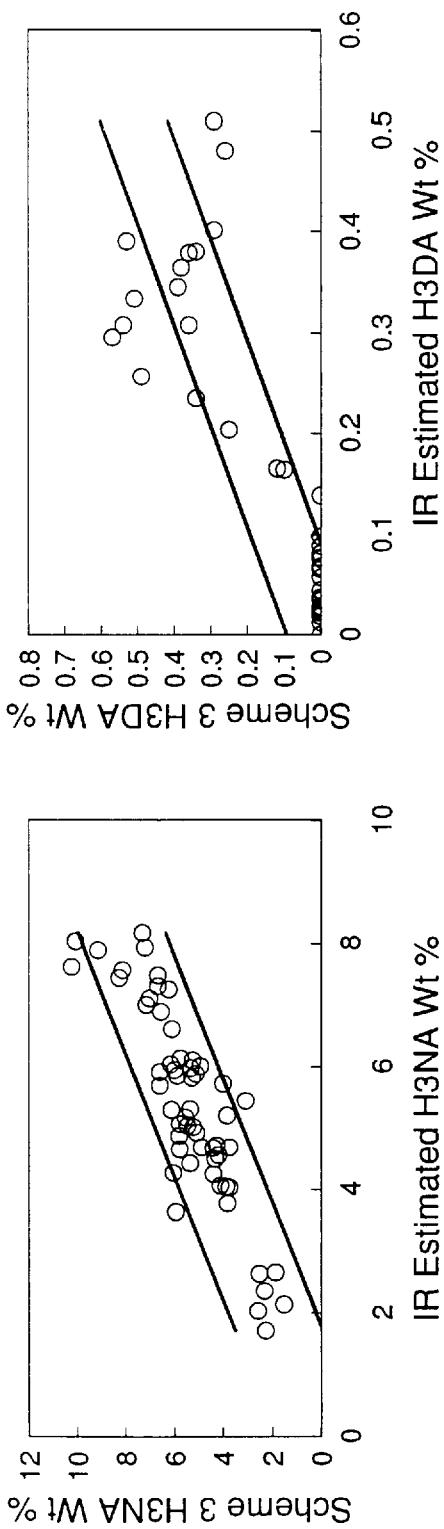
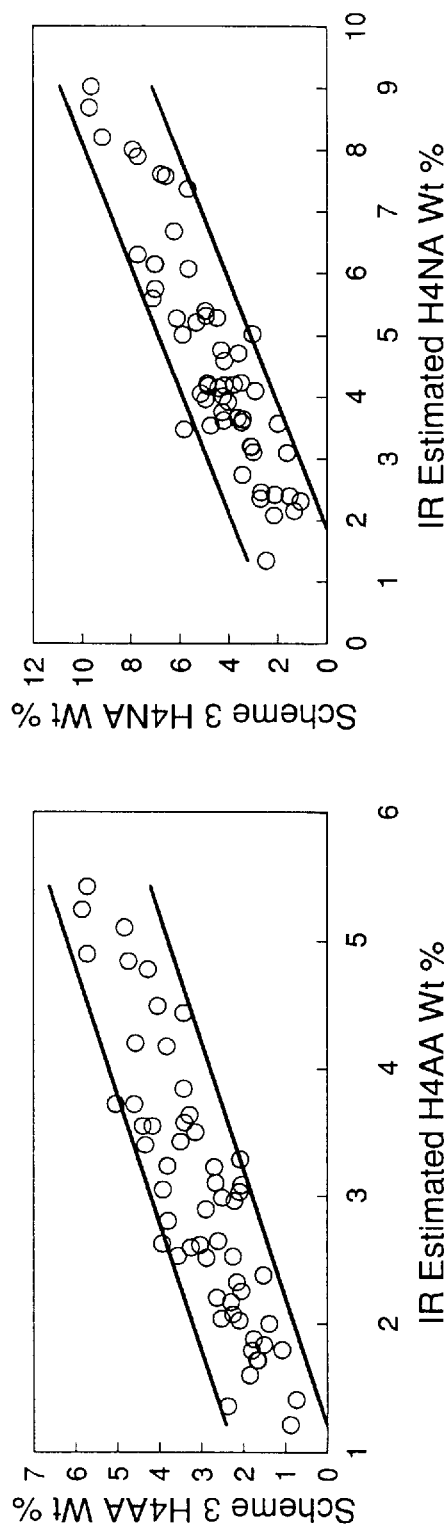
Fig. 2i
Fig. 2j
Fig. 2k
Fig. 2l

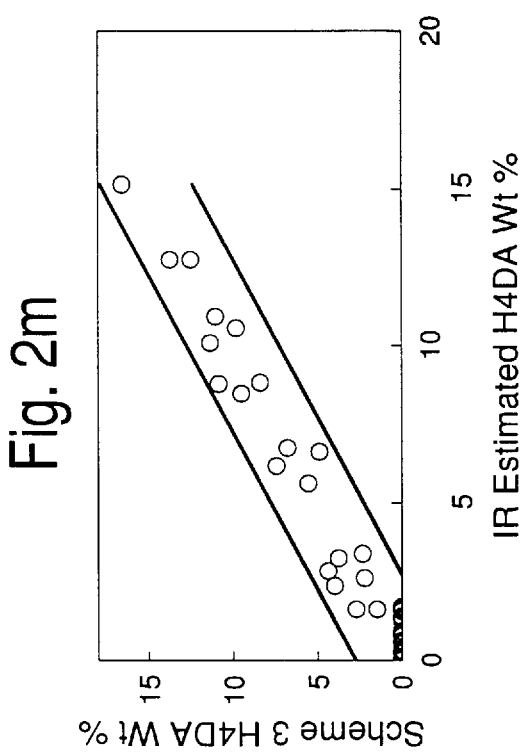

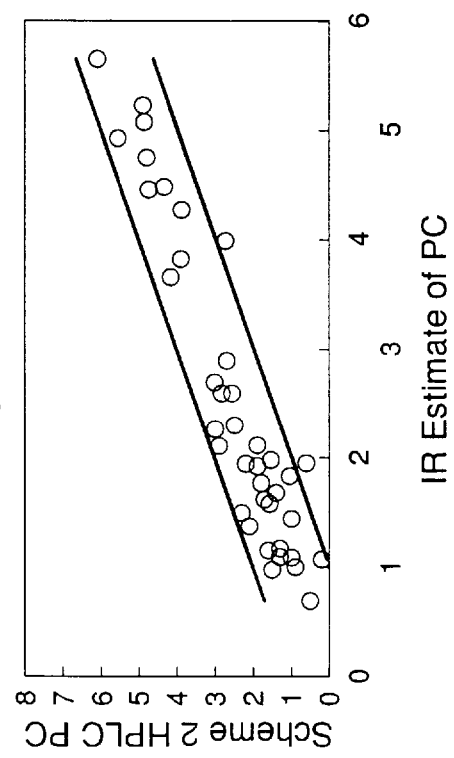

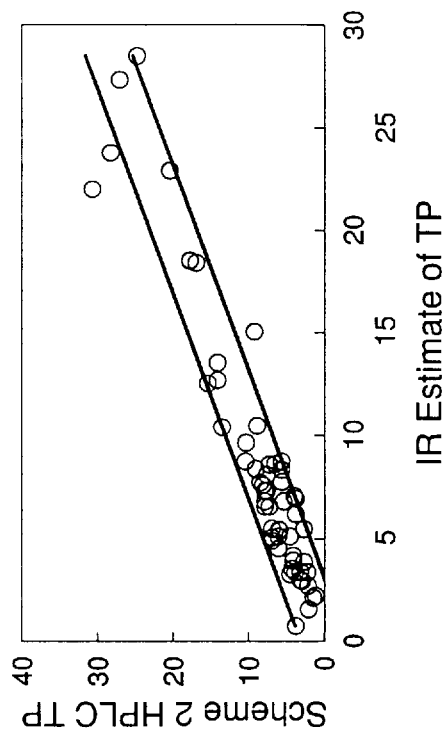
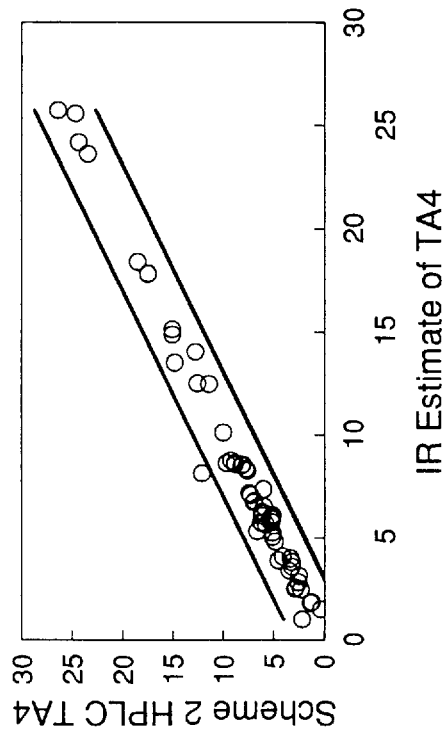
Fig. 7f
Fig. 7e

METHOD OF CHARACTERIZING FEEDS TO CATALYTIC CRACKING PROCESS UNITS

This is a continuation of application Ser. No. 08/731,040, filed Oct. 8, 1996, now abandoned, which is a continuation of application Ser. No. 08/385,257, filed Feb. 8, 1995, now abandoned.

FIELD OF THE INVENTION

BACKGROUND OF THE INVENTION

Optimization, design and control of catalytic cracking process units all benefit from kinetic models which describe the conversion of feeds to products. In order to properly describe the effects of changes in feed composition, such models require descriptions of the feed in terms of constituents which undergo similar chemical reactions in the cracking unit; these constituent groups are commonly called lumps. For design and optimization studies, a protocol which involves off-line feed analysis taking weeks or even months to provide a feed lump description may be adequate. However, for real time control of a process unit, a rapid and convenient method for characterization of the feeds to catalytic units is required. Current techniques for analysis of catalytic cracking feed components boiling above 650° F. include High Performance Liquid Chromatography (HPLC) sometimes coupled with Field-Desorption Mass Spectroscopy (FDMS). Both HPLC and FDMS are laboratory techniques which may require that a full range feed be prefractionated into appropriate boiling range fractions prior to analysis; as a result, analytical data are not available for several days after samples are obtained.

The present invention provides analysis of catfeeds in real time (a few minutes), online, and without requirements for feed prefractionation through Infrared Analysis of the whole catfeed sample and subsequent chemometric prediction of the feed components. The invention can also be employed for laboratory or at-line analyses of catfeeds. For example, the invention can be used to analyze samples from research reactors whose volumes are too small to allow for characterization by the distillation/HPLC/FDMS method. While the invention is principally used for real time analysis, control and optimization of a catalytic cracking unit, it could also be used to advantage for analysis, control and optimization of other petrochemical process units where lump based process models are employed. For example, the invention could be used to monitor changes in component lump concentrations across a hydrotreating unit, or across a lube extraction unit.

SUMMARY OF THE INVENTION

The present invention is a method to determine the chemical concentration of one or more of a number of the constituent classes of a feed to a catalytic cracking process. These constituent classes which are referred to as "lumps", include 14 different molecular types in 4 different boiling range fractions. A specific lump will include all individual molecular components which are expected to react in a similar way in the catalytic cracking unit.

The present invention is accomplished by:
(1) during a calibration step,
  (1a) analyzing a set of feed samples using an analysis scheme similar to Analysis Scheme 1, 2 or 3 described below to obtain molecular lumps;
  (1b) obtaining infrared spectra of the set of feed samples;
  (1c) correlating the molecular lumps to the infrared spectra to obtain a predictive model for each lump.
(2) during the analysis step,
  (2a) obtaining an infrared spectrum of an unknown feed;
  (2b) using said spectrum and the predictive model developed in
     (1c) to estimate molecular lumps for the feed;
(3) in the control/optimization step,
  (3a) using the molecular lump information generated in (2b) as input to a process model to control and/or optimize a process unit.

DESCRIPTION OF THE PREFERRED EMBODIMENT

Figure 1:
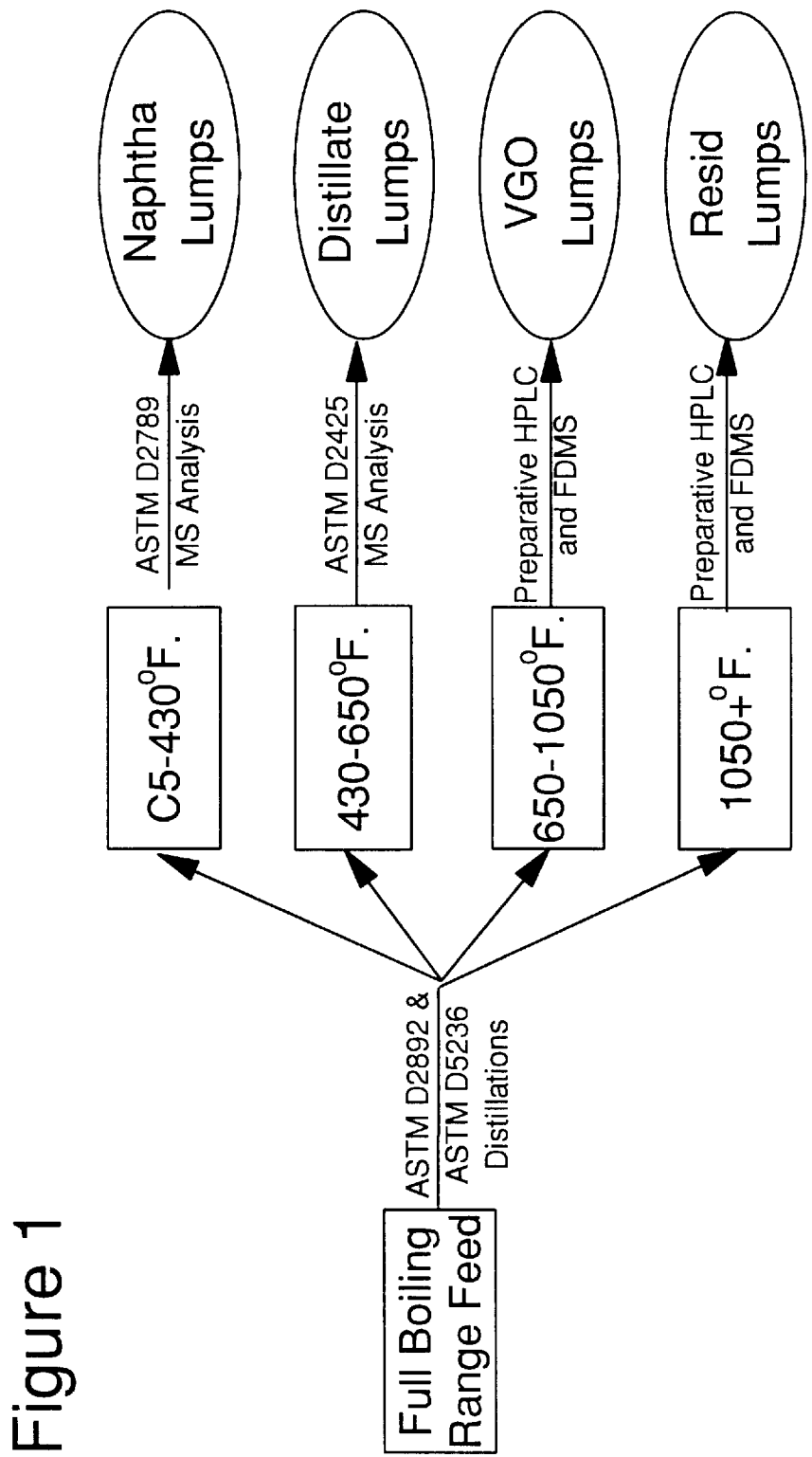
FIG. 1 shows a schematic of an analysis scheme referred to below as Analysis Scheme 1. This analysis scheme is used to determine component lumps of feeds to and/or products from hydrocarbon conversion, separation and blending process units.
Figure 2B:
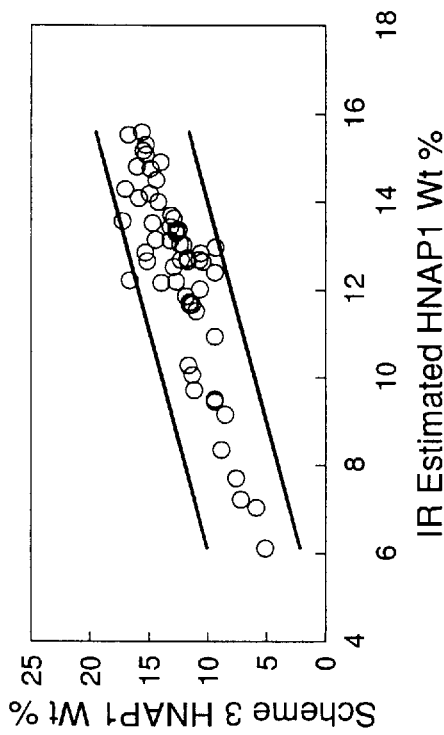
FIG. 2 shows plot of results for the calibration of the IR analysis of heavy (VGO) and resid) component lumps for example 1. Component lump abbreviations are from Table 1. The lines on each graph represent an estimate of the 95% confidence limits in the reference data against which the IR analysis is calibrated.
Figure 2D:
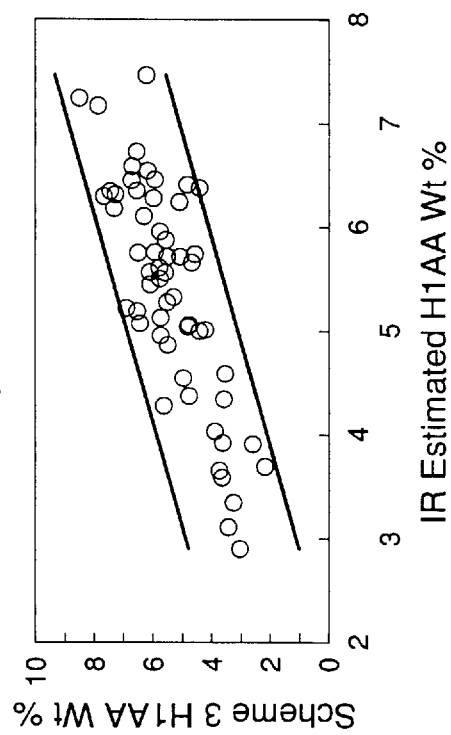
Figure 2A:
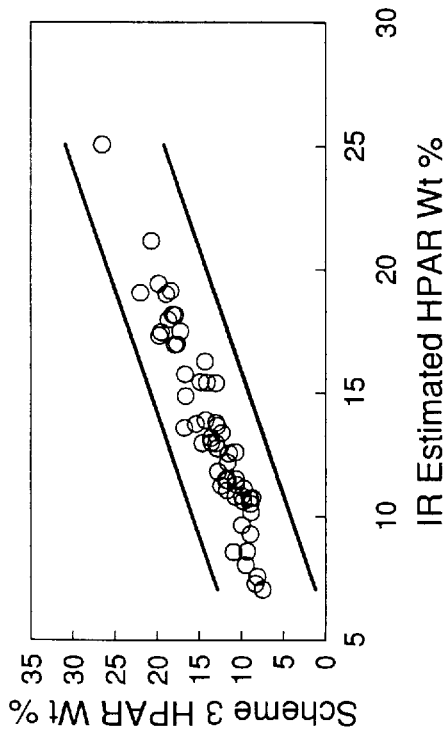
Figure 2C:
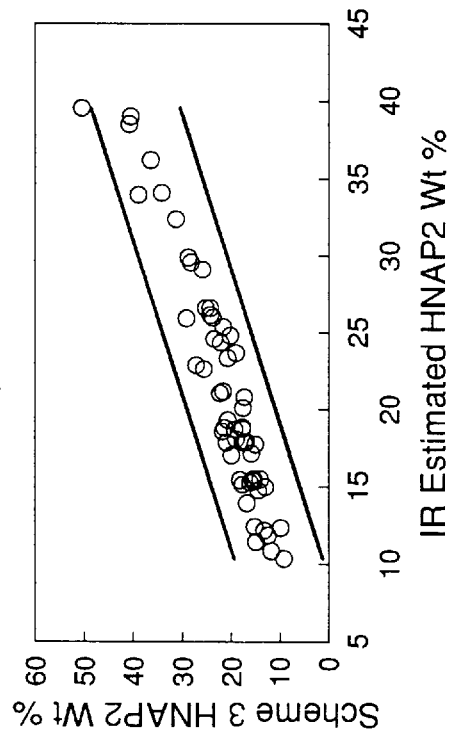
Figure 2F:
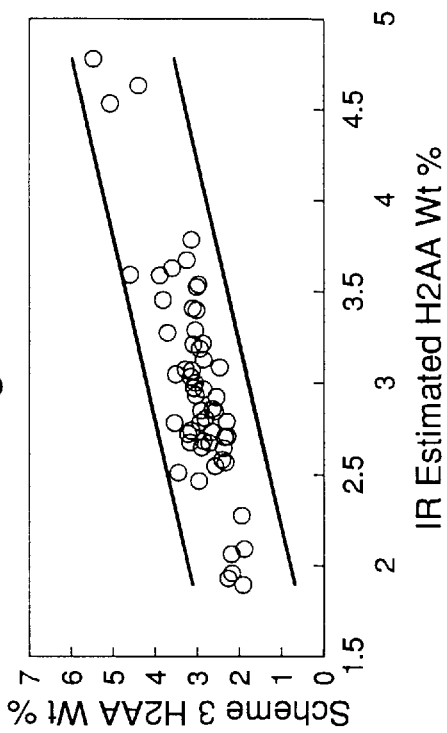
Figure 2H:
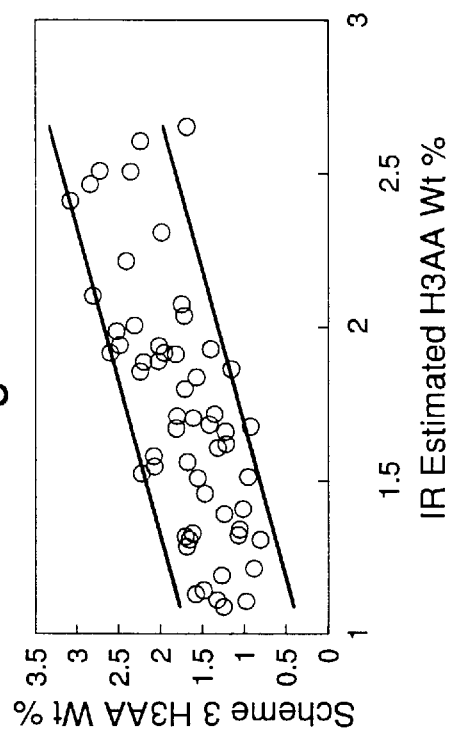
Figure 2E:
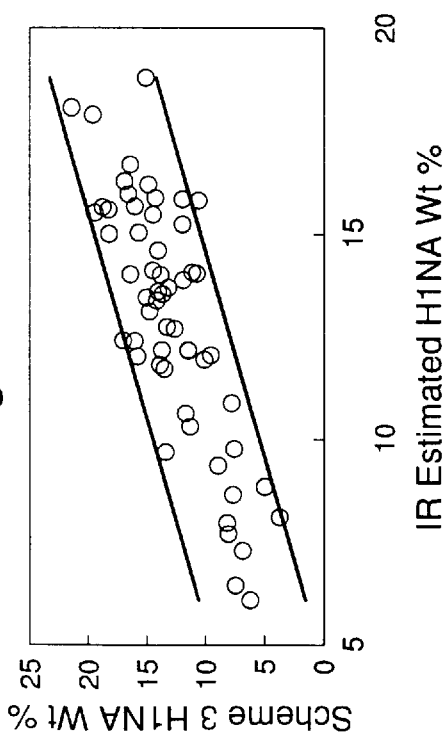
Figure 2G:
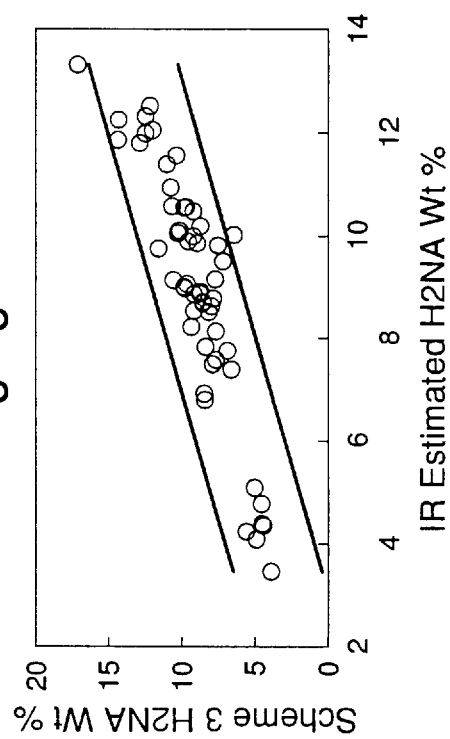
Figure 3A:
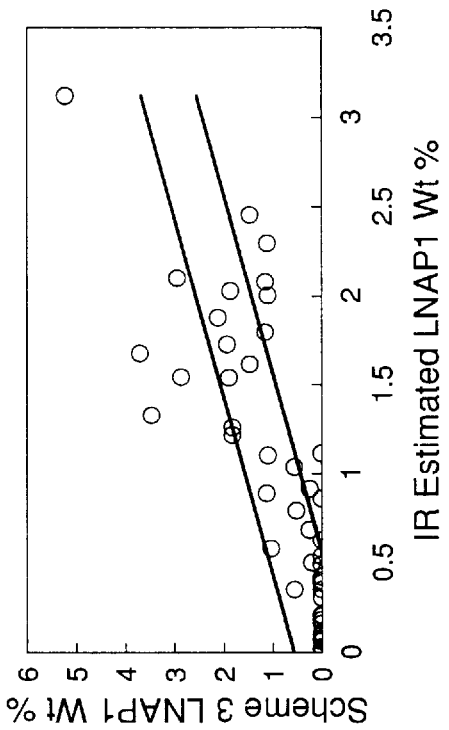
FIG. 3 shows plot of results for the calibration of the IR analysis of distillate component lumps for example 1. Component lump abbreviations are from Table 1. The lines on each graph represent an estimate of the 95% confidence limits in the reference data against which the IR analysis is calibrated.
Figure 3B:
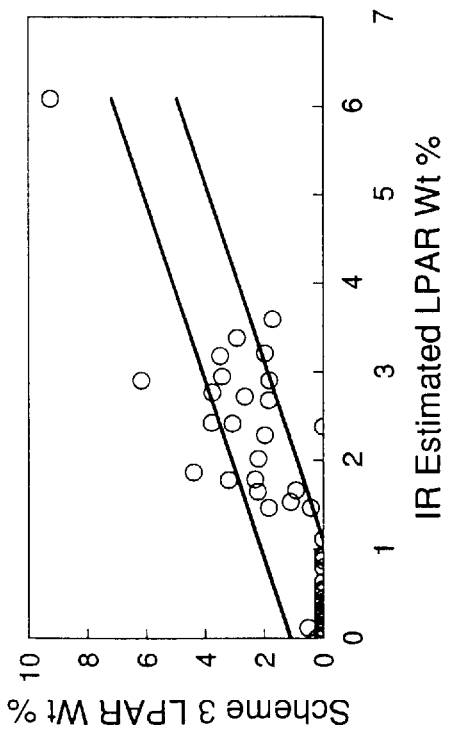
Figure 3C:
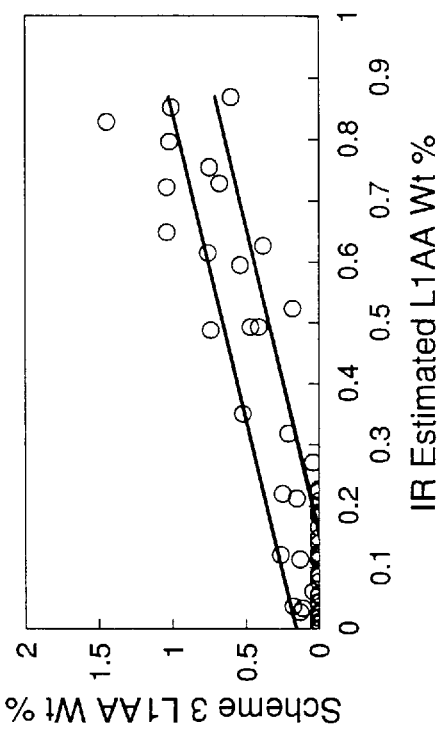
Figure 3D:
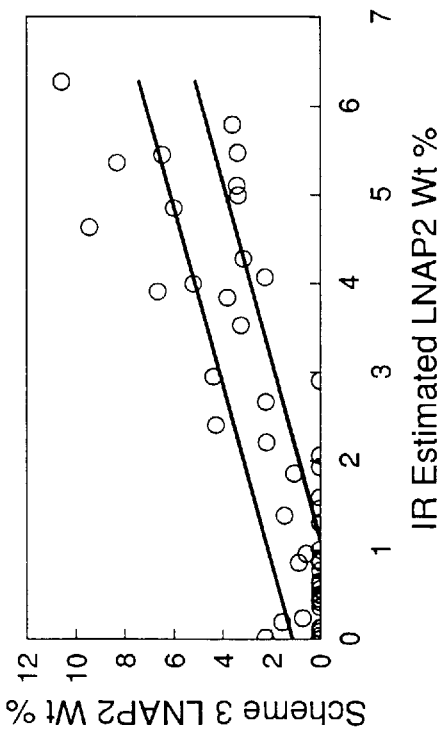
Figure 3F:
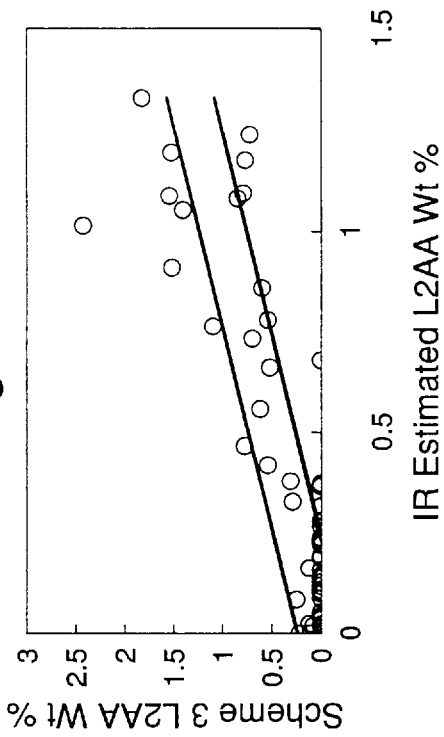
Figure 3H:
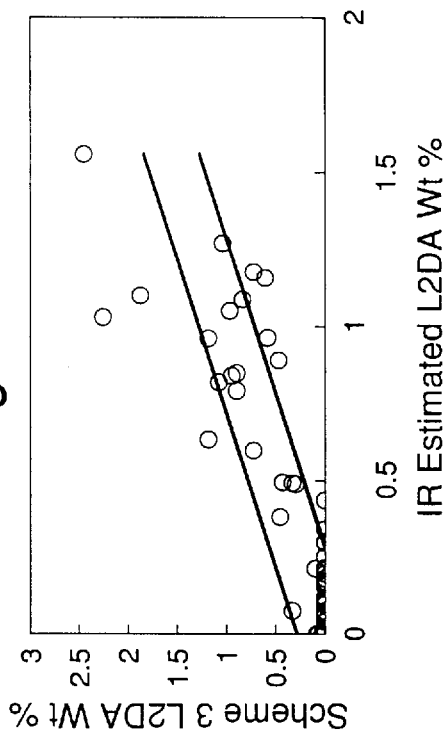
Figure 3E:
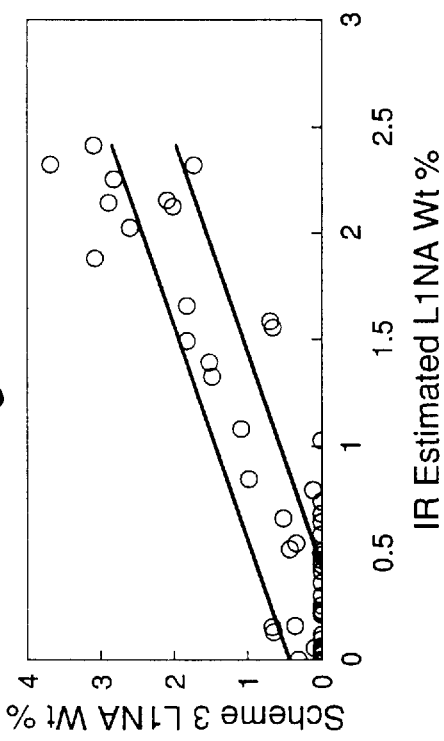
Figure 3G:
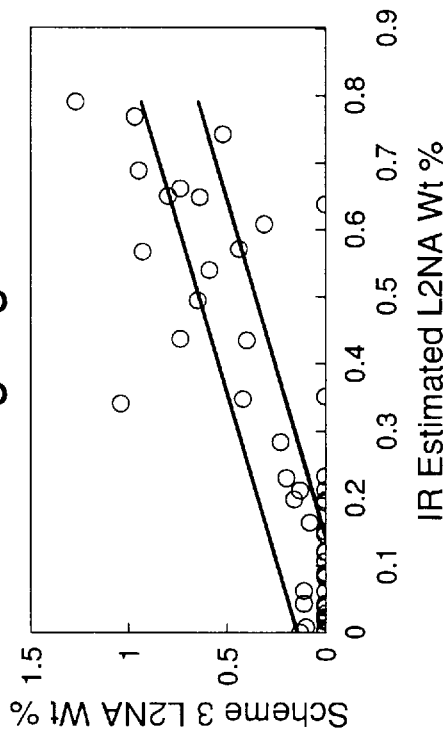
Figure 4B:
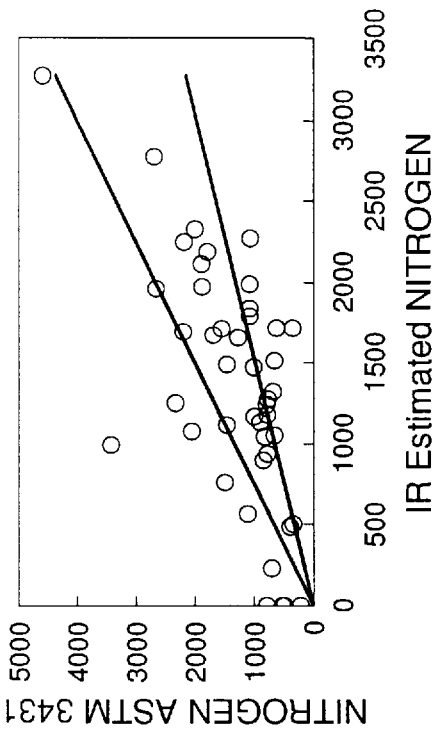
FIG. 4 show plots of results for the calibration of the IR analysis of elemental data (sulfur and nitrogen contents), microcarbon residue (MCR) measured as weight percent of resid, and feed density for example 1. The lines on each graph represent an estimate of the 95% confidence limits in the reference data against which the IR analysis is calibrated.
Figure 4D:
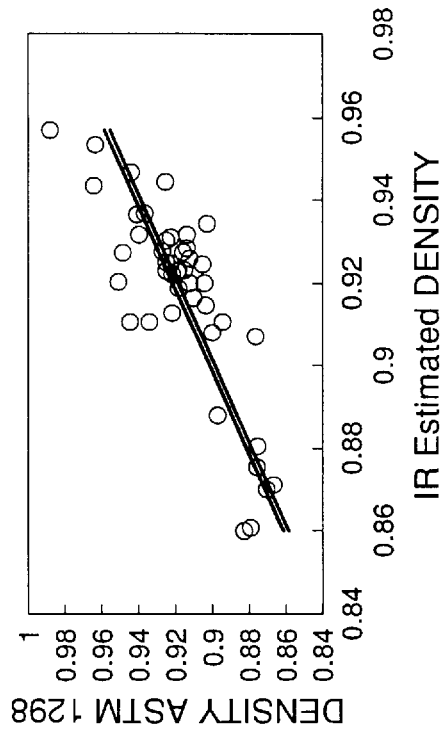
Figure 4A:
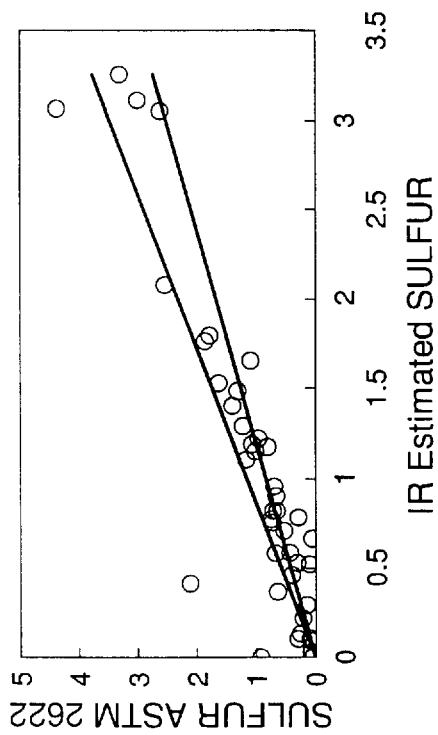
Figure 4C:
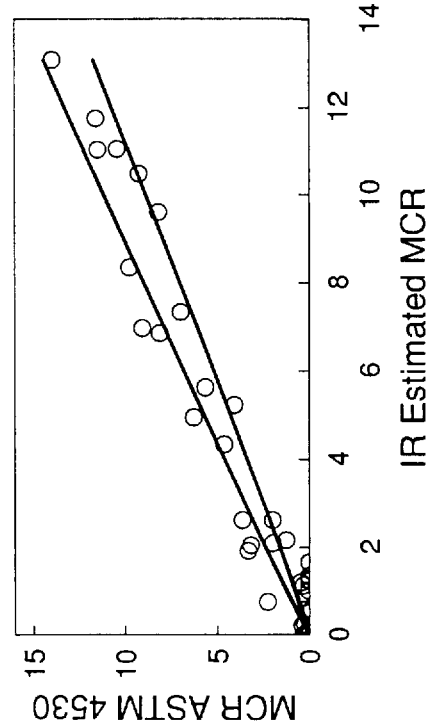
Figure 5A:
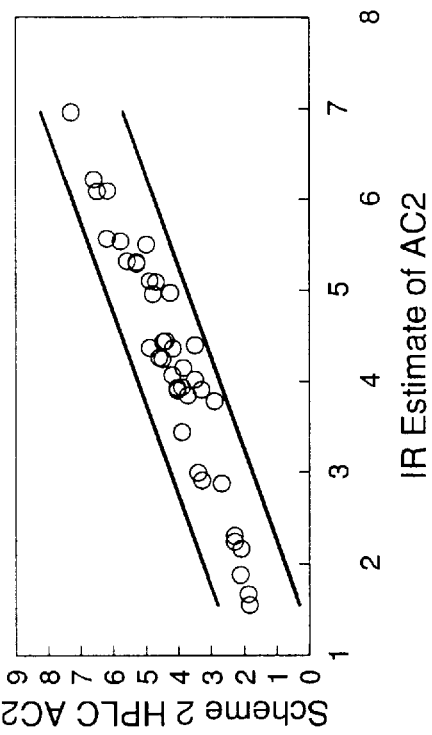
FIG. 5 shows plots of results for the calibration of the IR analysis of aromatic core data for example 2. The aromatic core reference data is obtained from HPLC analysis as described under Analysis Scheme 2 below. The abbreviations for the aromatic core lumps are given in Table 2. The lines on each graph represent an estimate of the 95% confidence limits in the reference data against which the IR analysis is calibrated.
Figure 5B:
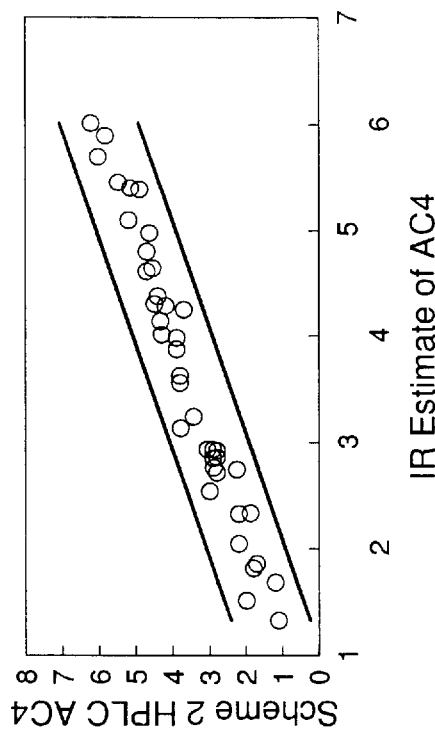
Figure 5C:
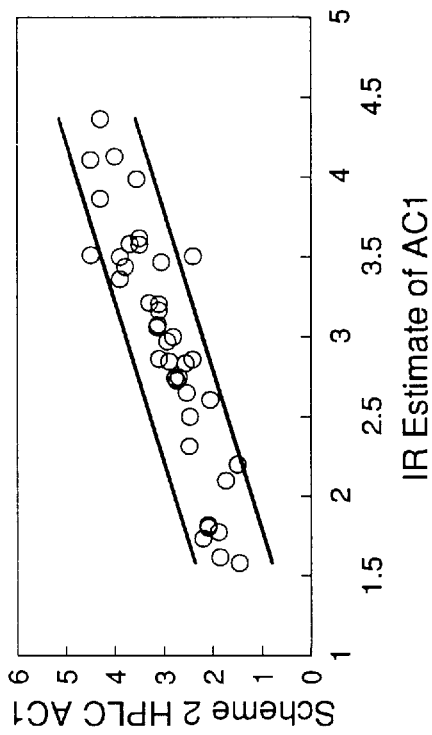
Figure 5D:
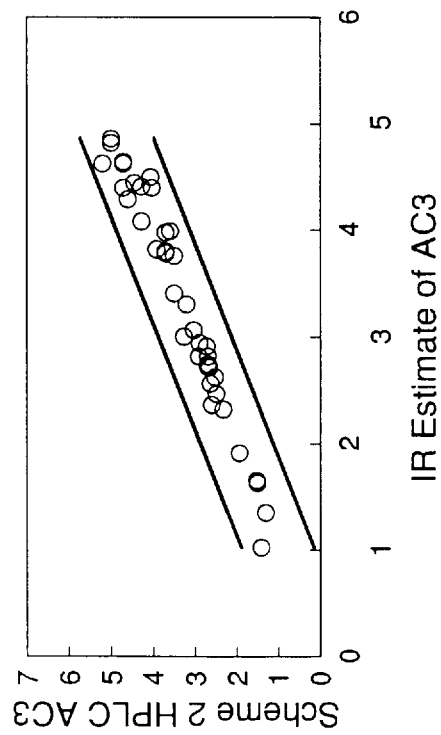
Figure 6B:
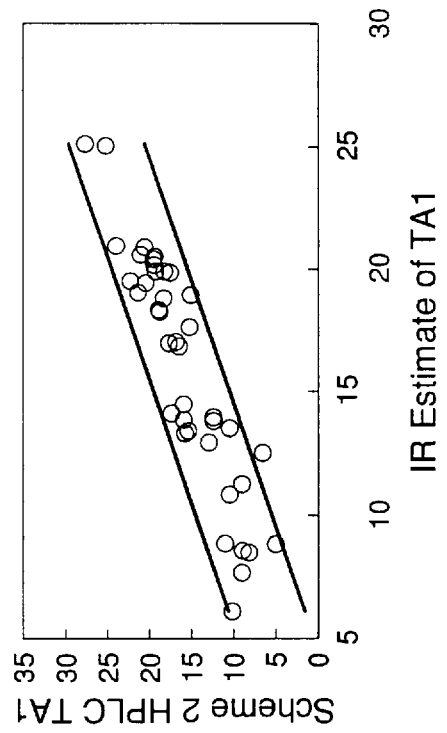
FIG. 6 show plots of results for the calibration of the IR analysis of HPLC mass data for example 2. The HPLC mass reference data is obtained from HPLC analysis as described under Analysis Scheme 2 below. The abbreviations for the mass lumps are given in Table 2. The lines on each graph represent an estimate of the 95% confidence limits in the reference data against which the IR analysis is calibrated.
Figure 6D:
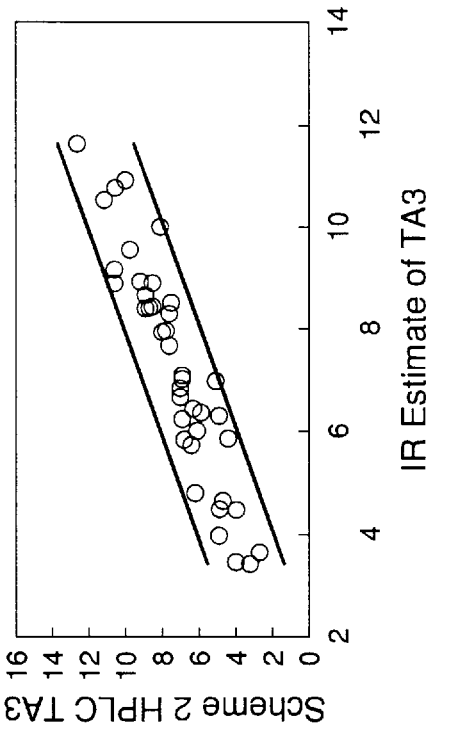
Figure 6A:
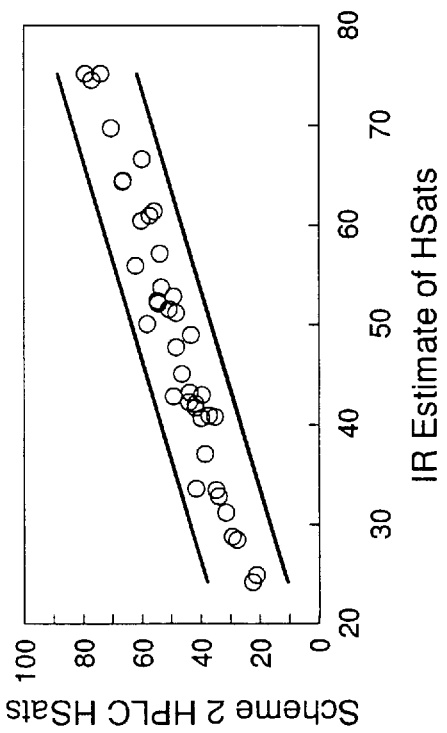
Figure 6C:
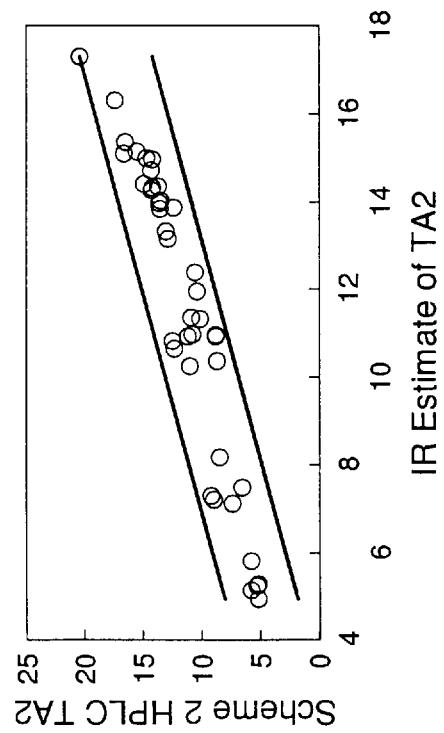
Figure 6F:
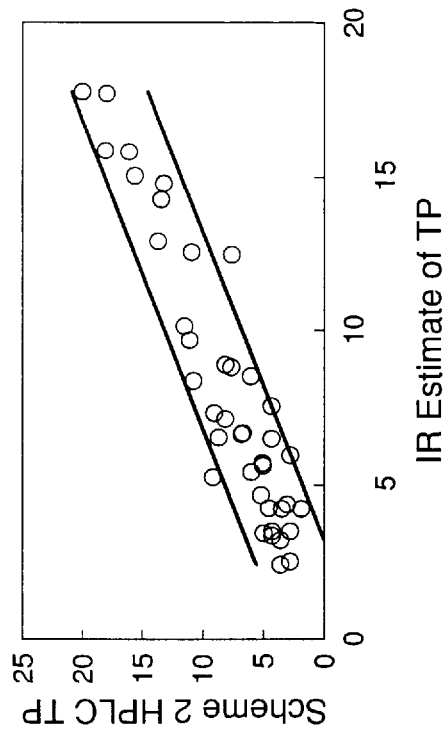
Figure 6E:
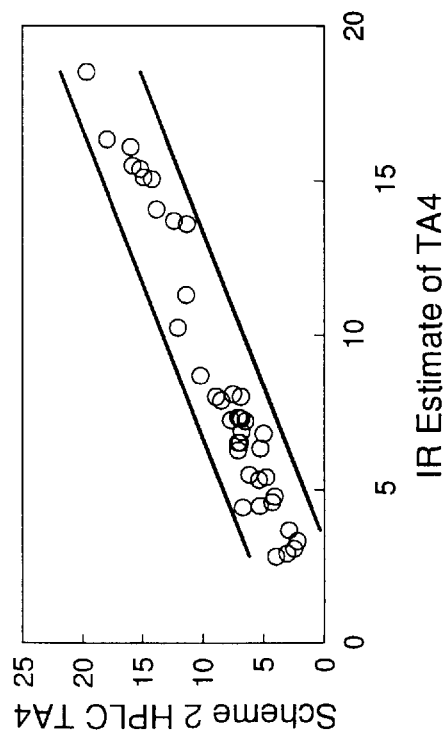
Figure 7A:
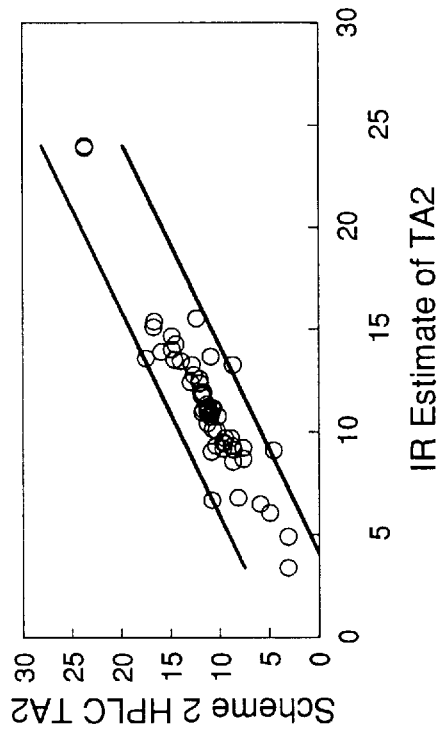
FIG. 7 show plots of results for the calibration of the IR analysis of HPLC mass data for example 3. The HPLC mass reference data is obtained from HPLC analysis as decribed under Analysis Scheme 2 below. The abbreviations for the mass lumps are given in Table 2. The lines on each graph represent an estimate of the 95% confidence limits in the reference data against which the IR analysis is calibrated.
Figure 7B:
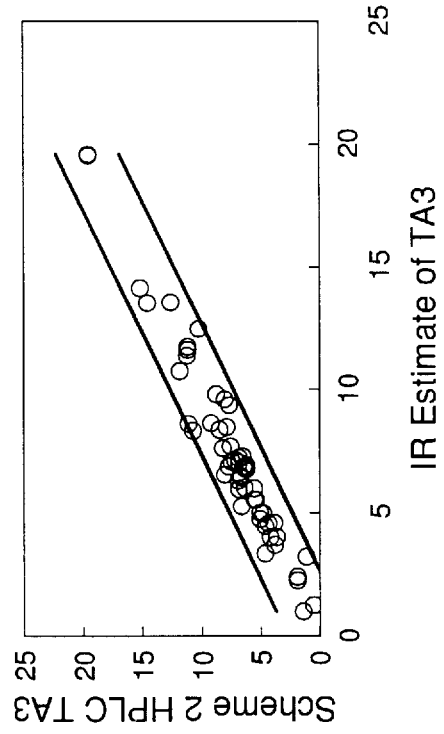
Figure 7C:
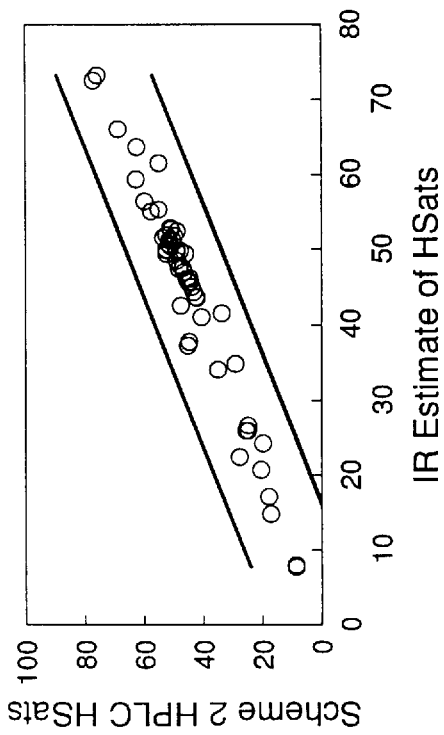
Figure 7D:
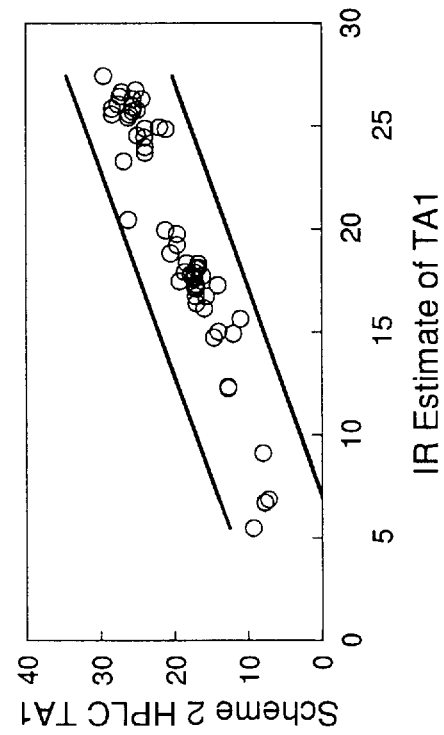
Figure 8A:
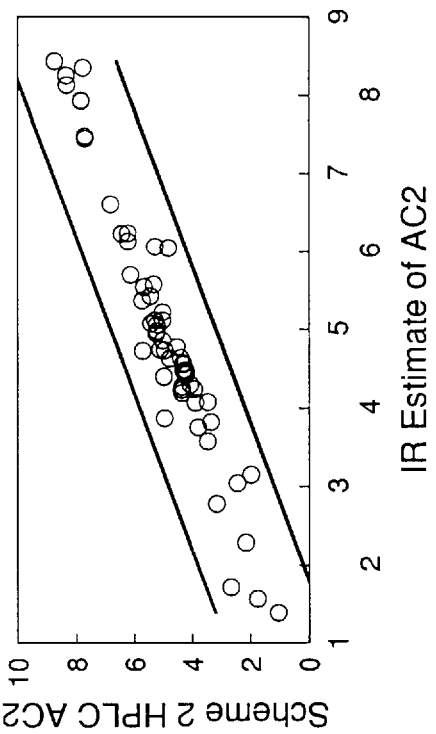
FIG. 8 shows plots of results for the calibration of the IR analysis of aromatic core data for example 3. The aromatic core reference data is obtained from HPLC analysis as described under Analysis Scheme 2 below. The abbreviations for the aromatic core lumps are given in Table 2. The lines on each graph represent an estimate of the 95% confidence limits in the reference data against which the IR analysis is calibrated.
Figure 8B:
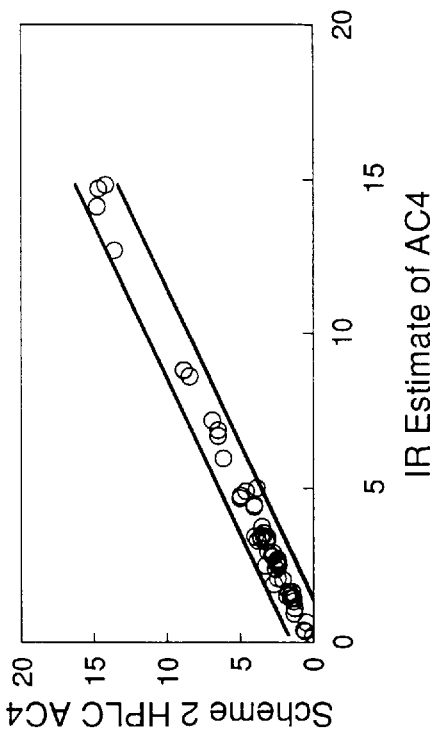
Figure 8C:
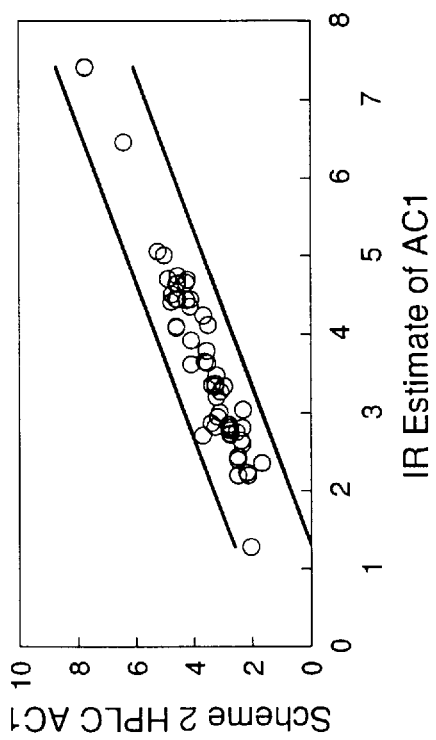
Figure 8D:
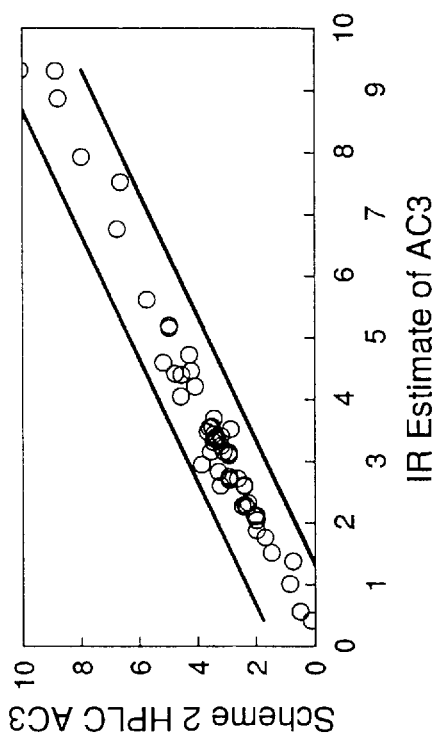
Figure 8E:
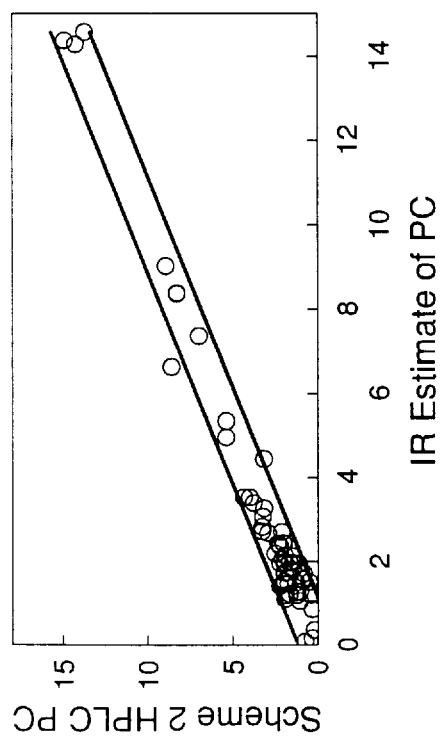

Optimization, design and control of catalytic cracking process units often accomplished using kinetic process models which describe the conversion of feeds to products. Since the feeds to such units are comprised of thousands of discrete molecular species, the development of kinetic equations for each molecular species is impractical. Instead, molecular species which undergo similar reactions are classified together in the development of the kinetic process model. These classes of molecular species are commonly referred to as lumps. To describe how changes in feed composition effect unit operation, feeds must be analyzed for their component lumps. In addition to molecular lumps, certain other feed qualities may also be included as inputs into process models including elemental data such as sulfur and nitrogen contents, physical inspections such as density, and reactivity measures such as micro carbon residue.

For design of the kinetic model and use of the model for off-line optimization studies, an off-line feed analysis protocol taking weeks or even months to provide a feed lump description may be adequate. However, for real time control of a process unit, a rapid and convenient method for on-line characterization of the feeds to catalytic units is required. Current techniques for analysis of catalytic cracking feed components boiling above 650° F. include High Performance Liquid Chromatography sometimes coupled with Field-Desorption Mass Spectroscopy. Both HPLC and FDMS are laboratory techniques that may require that a full range feed be prefractionated into appropriate boiling range fractions prior to analysis; as a result, analytical data are not available for several days after samples are obtained.

Feeds to catalytic units can include components with boiling points in the naphtha to vacuum resid range. To analyze such broad boiling range feeds in terms of lumped components that undergo similar reactions will generally require a sophisticated analytical scheme involving prefractionation of the feed into appropriate boiling range cuts and analysis of the cuts in terms of molecular component lumps. An example analytical scheme (Analysis Scheme 1) is shown in Figure I.

Analysis Scheme 1 involves fractionating the full boiling range feed into a $C_5$—430° F., naphtha cut, a 430° F.–650° F. distillate cut, a 650° F.–1050° F. vacuum gas oil cut, and a 1050° F.+ vacuum resid cut using standard 15/5 distillation and vacuum distillation procedures. The naphtha and distillate cuts are analyzed by standard mass spectroscopic analyses to obtain naphtha and distillate component lumps. The vacuum gas oil and vacuum resid cuts are first separated into fractions by preparative High Performance Liquid Chromatography, and then the HPLC fractions are further characterized by mass spectroscopic techniques such as Field Desorption Mass Spectroscopy. One HPLC technology suitable for separating feeds into appropriate fractions for subsequent MS analysis to produce molecular lumps has been described by Haberman, Overfeld and Robbins (J.I. Haberman, R.E. Overfeld, and W. K. Robbins, U.S. Pat. No. 4,988,446, Jan. 29, 1991). The types of molecular lumps typically obtained by an analysis scheme similar to that shown in FIG. 1 are listed in Table 1.

TABLE 1

MOLECULAR LUMPS OBTAINED FROM ANALYSIS SCHEME IN FIG. 1 NPAR. ETC. ARE ABBREVIATIONS FOR LUMP NAMES

| | Compositional Lump Naphtha Cut (C4-430° F.) | Distillate Cut (430° F.– 650° F.) | VGO Cut (650° F.– 1050° F.) | Resid Cut (1050° F.+) |
|---|---|---|---|---|
| Paraffins | NPAR | LPAR | HPAR | HPAR |
| Cyclic Olefins | NYCO | | | |
| Noncyclic Olefins | NNCO | | | |
| 1-Ring Naphthenes | NNAP1 | LNAP1 | HNAP1 | HNAP1 |
| 2-Ring Naphthenes | NNAP2 | LNAP2 | HNAP2 | HNAP2 |
| 1-Ring Alkyl Aromatics | N1AA | L1AA | H1AA | H1AA |
| 1-Ring Naphtheno-Aromatics | N1NA | L1NA | H1NA | H1NA |
| 2-Ring Alkyl Aromatics | | L2AA | H2AA | H2AA |
| 2-Ring Naphtheno-Aromatics | | L2NA | H2NA | H2NA |
| 2-Ring Denuded Aromatics | | L2DA | H2DA | H2DA |
| 3-Ring Alkyl Aromatics | | | H3AA | H3AA |
| 3-Ring Naphtheno-Aromatics | | | H3NA | H3NA |
| 3-Ring Denuded Aromatics | | | H3DA | H3DA |
| 4-Ring Alkyl Aromatics | | | H4AA | H4AA |
| 4-Ring Naphtheno-Aromatics | | | H4NA | H4NA |
| 4-Ring Denuded Aromatics | | | H4DA | H4DA |

Alkyl Aromatics are aromatics which contain only straight or branched substituent chains. NaphthenoAromatics are aromatics which contain one or more saturate rings in addition to possible straight or branched substituent chains. Denuded aromatics have no side chains larger than one methyl group. 2-Ring and 3-Ring Aromatics contain 2 and 3 aromatic rings per molecule. 4+ Ring Aromatics contain 4 or more aromatic rings per molecule. Polar fractions separated by the HPLC can be separately analyzed and included as polar lumps, or can be distributed across the other measured lumps. In addition to the molecular lumps, elemental data such as sulfur and nitrogen contents, physical inspections such as density, and reactivity measures such as micro carbon residue may be measured on total feeds and/or distillate cuts.

Because of the large number of fractionation steps and analyses required in the scheme shown in FIG. 1, the time required for obtaining the molecular lumps for a feed sample can be days to weeks. Data obtained in this fashion is used for design of the kinetic model, and for off-line calculations of optimum unit operating conditions, but it is not sufficiently timely to be used for the real time control and optimization of the process unit.

An alternative to Analysis Scheme 1 is to eliminate the mass spectroscopic analysis of the VGO and resid fractions and directly use analytical scale HPLC analyses of these fractions. The HPLC technology described by Haberman, Overfield and Robbins can provide total mass of aromatics, and aromatic core mass (mass in aromatic ring excluding substituents) through combined use of evaporative mass and UV diode array detectors. Analysis Scheme 2 is of particular advantage when feeds are limited to the VGO boiling range since it can be accomplished solely using HPLC. For full boiling range feeds, prefractionation of the feed prior to HPLC analysis, and MS analysis of the naphtha and distillate cuts are still required. The alternative Molecular lumps for VGO and Resids obtained from Analysis Scheme 2 (Table 2) are then used directly as inputs to a process model.

TABLE 2

MOLECULAR LUMPS FOR VGOs ANO RESIDS OBTAINED BY HPLC

| Compositional Lump | VGO Cut and/or Resid Cut (650° F.–1050° F. & 1050° F.+) |
|---|---|
| Saturates | HSats |
| Total 1-Ring Aromatics | TA1 |
| 1-Ring Aromatic Cores | AC1 |
| Total 2-Ring Aromatics | TA2 |
| 2-Ring Aromatic Cores | AC2 |
| Total 3-Ring Aromatics | TA3 |
| 3-Ring Aromatic Cores | AC3 |
| Total 4+Ring Aromatics | TA4 |
| 4+Ring Aromatic Cores | AC4 |
| Total Polars | TP |
| Polar Cores | PC |

The mass spectral analyses of the VGO and Resid cuts required by the analysis scheme in FIG. 1 add significantly to the time and cost of the total analysis. The MS analysis does, however, provide additional molecular breakdown of the feed that can be useful in modeling the process. A third alternative (Analysis Scheme 3) is to correlate the molecular lumps obtained from Analysis Scheme 1 (preparative scale HPLC plus MS) to the lumps from Analysis Scheme 2 (HPLC with mass and UV detection) for a set of feeds, and then to use those correlations to convert results from Analysis Scheme 2 into the molecular lumps which would have been obtained by Scheme 1. The correlations can be accomplished using only the HPLC mass and core lumps, or they can be augmented by additional analytical tests. For instance, API gravity (ASTM D287), elemental data, or micro-carbon residue (D4530) data on VGO or resid cuts could be used as independent variables in addition to the HPLC mass and core lumps to correlate to Scheme 1 lumps as dependent variables.

Regardless of which analysis scheme is used, the time required to prefractionation the feed into boiling range cuts, and to analyze the cuts by MS and/or HPLC will be on the order of days to weeks. The analyses are thus not suited to on-line analysis, control and optimization. The present invention seeks to address this problem though the use of infrared analysis to replace these analytical schemes.

The use of infrared analysis in process control has been discussed by several authors. None have used infrared to obtain detailed compositional lump information on petrochemical feeds as complex as cat feeds.

Espinosa, Lambert, Martens and Ventron (European Patent Application 0304232, 11.08.88) describe the use of Near-Infrared spectroscopy to determine the properties and/or yield of a product from a hydrocarbon conversion or separation process. Unlike the current invention, their method works by correlating the spectrum of a feed directly to the property and/or yield of product without the use of a process model. Their invention cannot be used with a complex kinetic process model, and is applicable only to processes at the same fixed conditions as were used in developing the correlation.

Maggard (U.S. Pat. No. 5,349,189, Sep. 20, 1994) describes the use of Near-Infrared to measure gross molecular grouping or classes such as paraffins, isoparaffins, aromatics, naphthenes and olefins (PIANO). Maggard does not demonstrate that his technique is applicable for hydrocarbons other than gasolines (naphthas), and does not provide the differentiation of aromatics and naphthenes by ring size that the current invention provides.

Maggard (U.S. Pat. No. 5,348,645, Sep. 20, 1994) describes the use of Near-Infrared for controlling organic sulfur content of a hydrocarbon product from a sulfur-removal process of a blending process. Maggard's measurements are conducted in a different spectral region from the present invention.

The present invention is accomplished by:
(1) during a calibration step,
 (1a) analyzing a set of feed samples using an analysis scheme similar to Analysis Scheme 1, 2 or 3 described above to obtain molecular lumps;
 (1b) obtaining infrared spectra of the set of feed samples;
 (1c) correlating the molecular lumps to the infrared spectra to obtain a predictive model for each lump.
(2) during the analysis step,
 (2a) obtaining an infrared spectrum of an unknown feed;
 (2b) using said spectrum and the predictive model developed in
  (1c) to estimate molecular lumps for the feed;
(3) in the control/optimization step,
 (3a) using the molecular lump information generated in (2b) as input to a process model to control and/or optimize a process unit.

The spectra in steps (1b) and (2a) are preferably collected over the extended mid-infrared spectral range of 7000 to 400 cm$^{-1}$. The spectra may be collected using cells with calcium fluoride windows to contain the feeds which have nominal pathlengths of approximately 0.5 millimeters, in which case the spectral range will preferably be from 6700 to 1720 cm$^{-1}$. Alternatively, for laboratory analysis, cells with potassium bromide windows and nominal 0.05 millimeter pathlengths may be employed, in which case the spectral range will preferably be from 3800 to 400 cm$^{-1}$. Other sampling techniques such as attenuated total reflection (ATR) could also be used in the collection of the spectra over all or part of the extended mid-infrared range.

Preferably, the extended mid-infrared spectra are obtained using Fourier Transform Infrared (FT-IR) instrumentation. Spectra are preferably collected at 2 cm$^{-1}$ resolution, although other resolutions could also be employed.

During the collection of the extended mid-infrared spectra, the feed samples are maintained at a temperature sufficient to ensure flow of the feed through the cell. Flow may be interrupted during the spectral measurement as would be typically done for laboratory application, or may be continuous during the spectral measurement. Temperatures in the range of 60° C. could typically be employed, although higher or lower temperatures can also be used providing that they are high enough to ensure flow of the feed, and low enough to prevent thermal reaction of the feed during measurement. Temperatures will preferably be maintained to within ±5° C. of the nominal temperature during the spectral measurement.

The correlation in step (1c) is accomplished using any one of several chemometric methods including MultiLinear Regression (MLR), Partial Least Squares (PLS), Principal Components Regression (PCR), or Constrained Principal Spectra Analysis (CPSA). CPSA which is described by Brown in U.S. Pat. No. 5121337 (Jun. 9, 1992) is the preferred means of obtaining the correlations.

Example 1:
Estimation of Compositional Lumps for Catfeeds Boiling above 430° F. via Correlation of Extended FT-MIR Spectral Data to Data from Analysis Scheme 3.

Spectra for 74 catfeeds boiling about 430° F. were measured over the 7000–400 cm$^{-1}$ extended mid infrared range using a FT-IR spectrometer operating at 2 cm$^{-1}$ resolution. A cell with 0.5 millimeter pathlength and calcium fluoride windows which was thermostated at 60±1° C. was employed for the spectral measurement. Two calibrations were developed for molecular lumps, elemental data, physical inspections and reactivity measures of the feed and feed fractions using Constrained Principal Spectra Analysis (CPSA). The parameters used in the calibrations were as follows:

Spectral range:
  Calibration 1- Spectral absorbance values in the frequency ranges from 6700 to 3100 cm$^{-1}$ and from 2600 to 1720 cm$^{-1}$ were used in a CPSA model. The region from 3100 to 2600 cm$^{-1}$ and below 1720 cm$^{-1}$ are excluded since the absorptions occurring in these regions are beyond the linear dynamic range of the FT-IR spectrometer.
  Calibration 2- Spectral absorbance values in the frequency ranges from 5524 to 5155 cm$^{-1}$, 4999 to 4860 cm$^{-1}$, 4694 to 3100 cm$^{1}$ and 2600 to 1720 cm$^{-1}$ where used in a CPSA model. Maggard (U.S. Pat. No. 5349188 had used at least one of the various absorption bands occurring across the Near Infrared (NIR) range from 824–1810 mm (12136–5525 cm$^{-1}$), from 1940–2000 nm (5155–5000 cm$^{-1}$) and from 2058–2130 mm (4859–4695 cm$^{-1}$) sometimes in combination with absorptions in the region from 2064–2234 mm (4845–4476 cm$^{-1}$) to measure PIANO components in gasolines. The NIR measurements conducted by Maggard require thicker cell pathlengths (2–10 millimeter) than are used in the present invention to obtain absorptions in the overlapped regions which are sufficiently intense to be useful in the calibrations. To demonstrate that the absorptions used by Maggard do not contribute to the calibrations of the present invention, the regions from 6700–5525 cm$^{-1}$, from 5155–5000 cm$^{-1}$ and from 4860–4695 cm$^{-1}$ were excluded from calibration 2.

Corrections:
  Calibration 1- Quadratic polynomial corrections were employed in the CPSA models to compensate for baseline variations. Two sets of polynomials were generated, one spanning 6700 to 3100 cm$^{-1}$ and one spanning 2600 to 1720 cm$^{-1}$. Water vapor corrections were also included to compensate for variations in the spectrometer purge.
  Calibration 2- Quadratic polynomial corrections were employed in the CPSA models to compensate for baseline variations. Two sets of polynomials were generated, one spanning 5524 to 3100 cm$^{-1}$ and one spanning 2600 to 1720 cm$^{-1}$. Water vapor corrections were also included to compensate for variations in the spectrometer purge.

Regression:
  Both Calibrations- A press based stepwise regression procedure was used in developing the CPSA models. A maximum of 14 constrained principal components was retained in each case.

Results for the two calibrations are shown in Table 3. Abbreviations in Table 3 are from Table 1. Calibrations were developed for the distillate lumps and heavy (VGO and Resid) lumps as well as for feed sulfur and nitrogen content, micro, carbon residue of the resid fraction, and specific gravity of the feed. In the majority of the calibrations, there is no statistically significant difference between the Standard Errors of Estimate (SEE) obtained for calibrations 1 and 2 (F values <1.53 based on 60 degrees of freedom in both models). For those components that show a statistically significant difference in SEE (F values >1.54), the SEE for calibration 2 was always smaller than that for calibration 1. Clearly, the absorptions used in the Maggard patent do not contribute to the correlations on which the current invention is based.

FIG. 2 shows plots of calibration results for the heavy (VGO and resid) component lumps. FIG. 3 shows similar plots for distillate lumps. FIG. 4 shows plots for elemental data, micro carbon residue measured as wt % of resid, and feed density. In each case, the lines on the graph are an estimate of the reproducibility of the reference method data. Abbreviations in FIGS. 2–4 are from Table 1.

TABLE 3

| Component wt % | Calibration 1 SEE | PRESS | Calibration 2 SEE | PRESS | F Value |
|---|---|---|---|---|---|
| H1AA | 0.931 | 0.986 | 0.928 | 0.980 | 1.00 |
| H1NA | 2.537 | 2.723 | 2.586 | 2.737 | 1.04 |
| H2AA | 0.449 | 0.485 | 0.427 | 0.477 | 1.11 |
| H2NA | 1.447 | 1.510 | 1.338 | 1.398 | 1.17 |
| H3AA | 0.412 | 0.441 | 0.407 | 0.440 | 1.02 |
| H3DA | 0.129 | 0.138 | 0.101 | 0.109 | 1.65 |
| H3NA | 1.112 | 1.228 | 1.041 | 1.211 | 1.14 |
| H4AA | 0.678 | 0.812 | 0.671 | 0.780 | 1.02 |
| H4DA | 1.165 | 1.336 | 1.153 | 1.317 | 1.02 |
| H4NA | 0.954 | 1.143 | 0.970 | 1.102 | 1.04 |
| HNP1 | 1.723 | 1.927 | 1.649 | 1.744 | 1.09 |
| HNP2 | 3.107 | 3.536 | 3.031 | 3.357 | 1.05 |
| HPAR | 1.339 | 1.417 | 1.310 | 1.504 | 1.04 |
| L1AA | 0.266 | 0.275 | 0.171 | 0.186 | 2.40 |
| L1NA | 0.751 | 0.795 | 0.476 | 0.522 | 2.49 |
| L2AA | 0.415 | 0.441 | 0.306 | 0.329 | 1.84 |
| L2DA | 0.426 | 0.448 | 0.297 | 0.321 | 2.06 |
| L2NA | 0.264 | 0.276 | 0.190 | 0.210 | 1.94 |
| LNP1 | 0.864 | 0.908 | 0.634 | 0.677 | 1.86 |
| LNP2 | 2.004 | 2.089 | 1.392 | 1.532 | 2.07 |
| LPAR | 1.322 | 1.416 | 0.940 | 1.066 | 1.98 |
| SULFUR ppm | 0.575 | 0.600 | 0.424 | 0.466 | 1.84 |
| NITROGEN wt% on resid | 813 | 871 | 778 | 845 | 1.09 |
| MCR | 0.980 | 1.238 | 1.112 | 1.349 | 1.29 |
| grams/cc DENSITY | 0.0192 | 0.0201 | 0.0153 | 0.0172 | 1.57 |

Example 2:
Estimation of Component Lumps for Catfeeds Boiling above 650° F. via Correlation of Extended FT-MIR Spectral Data to Data from Analysis Scheme 2.

Spectra for 40 catfeeds boiling above 650° F. were measured over the 7000–400 cm$^{-1}$ extended mid infrared range using a FT-IR spectrometer operating at 2 cm$^{-1}$ resolution. A cell with 0.5 millimeter pathlength and calcium fluoride windows which was thermostated at 60±1° C. was employed for the spectral measurement. Two calibrations were developed for molecular lumps, elemental data, physical inspections and reactivity measures of the feed and feed fractions using Constrained Principal Spectra Analysis (CPSA). The parameters used in the calibrations were identical to those used in calibration 2 in example 1.

Results for the calibration are shown in Table 4, and plotted in FIGS. 5–6. Abbreviations in Table 4 and in FIGS. 5–6 are from Table 2.

TABLE 4

| HPLC Component | SEE | PRESS |
|---|---|---|
| AC1 | 0.415 | 0.460 |
| AC2 | 0.430 | 0.501 |
| AC3 | 0.295 | 0.436 |
| AC4 | 0.396 | 0.474 |
| PC | 0.583 | 0.716 |
| TP | 2.020 | 2.288 |
| HSats | 4.147 | 4.649 |
| TA1 | 3.443 | 3.932 |
| TA2 | 1.372 | 1.665 |
| TA3 | 0.957 | 1.053 |
| TA4 | 1.163 | 1.450 |

Example 3:
Estimation of Component Lumps for Catfeeds Boiling above 650° F. via Correlation of FT-MIR Spectral Data to Data from Analysis Scheme 2.

FT-MIR Spectra of 50 catfeeds having initial boiling points nominally greater than 650° F. were measured over the range of 4000–400 cm$^{-1}$ mid infrared range using a FT-IR spectrometer operating at 2 cm$^{-1}$ resolution. A cell with 0.05 millimeter pathlength and potassium bromide windows which was thermostated at 60±1° C. was employed for the spectral measurement. A calibration was developed for molecular lumps of the feeds using Constrained Principal Spectra Analysis (CPSA). The parameters used in the calibrations were as follows:

Spectral range:
  Spectral absorbance values in the frequency ranges from 3800 to 2995 cm$^{-1}$, 1935 to 1550 cm$^{-1}$, and from 1400 to 600 cm$^{-1}$ were used in a CPSA model. The region from 2995 to 1935 cm$^{-1}$ and from 1550 to 1400 cm$^{-1}$ were excluded since the absorptions occurring in these regions are beyond the linear dynamic range of the FT-IR spectrometer.

Corrections:
  Linear polynomial corrections were employed in the 3800 to 2995 cm$^{-1}$ and 1935 to 1550 cm$^{-1}$ regions and quadratic polynomial corrections in the 1400 to 600 cm$^{-1}$ region in the CPSA models to compensate for baseline variations. Water vapor corrections were also included to compensate for variations in the spectrometer purge.

Regression:
  Both Calibrations -A stepwise regression procedure was used in developing the CPSA models. A maximum of 12 constrained principal components was retained in each case.

The results for the calibration are shown in Table 5. FIG. 7 shows comparisons of results for analyses by scheme 2 versus IR estimates for component lump weights, and FIG. 8 shows similar comparisons for aromatic cores. Abbreviations in Table 5 and in FIGS. 7–8 are from Table 2.

TABLE 5

|  | SEE | PRESS |
|---|---|---|
| HSATS | 3.173 | 3.626 |
| TA1 | 1.963 | 2.570 |
| TA2 | 1.600 | 1.935 |
| TA3 | 0.976 | 1.135 |
| TA4 | 0.871 | 0.908 |
| TP | 2.400 | 3.138 |
| AC1 | 0.376 | 0.483 |
| AC2 | 0.466 | 0.629 |
| AC3 | 0.348 | 0.436 |
| AC4 | 0.380 | 0.525 |
| PC | 0.602 | 0.710 |

Example 4:
Control of FCCU and Hydrotreating Units

Figure 9:
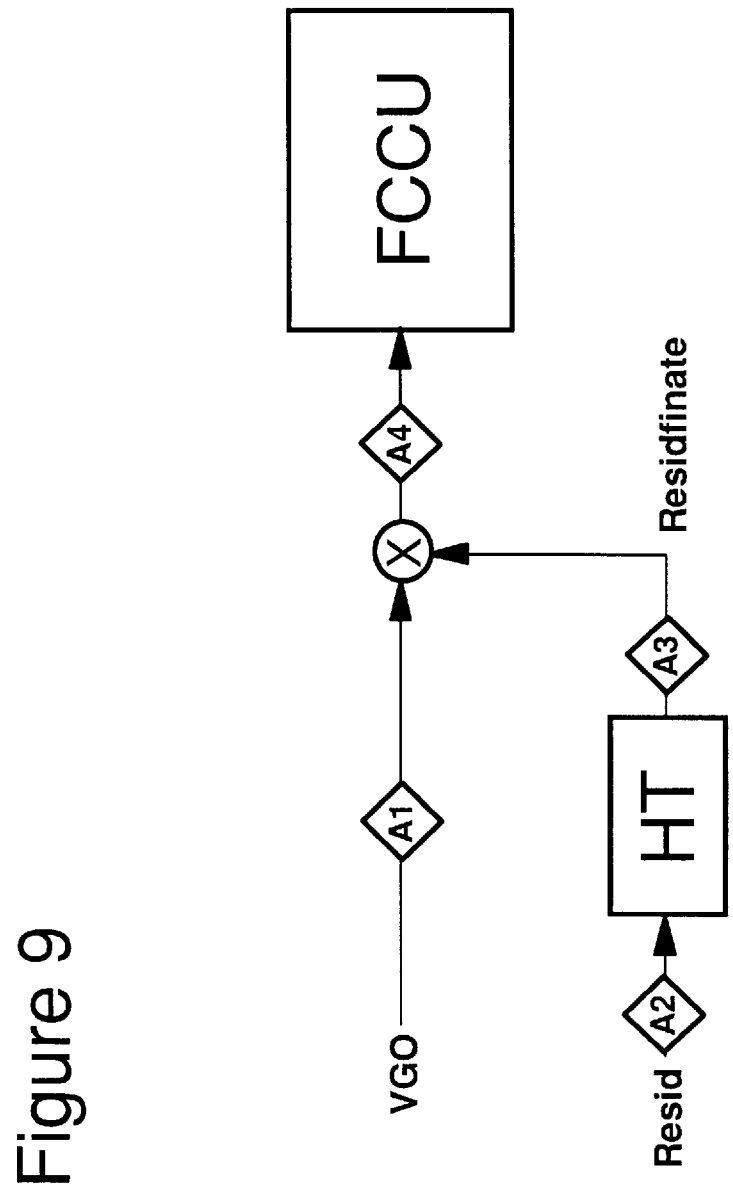
FIG. 9 shows a diagram of a refinery operation discussed in example 4. Vacuum residue (Resid) is processed in a hydrotreating unit (HT) to produce hydrotreated vacuum residue (Residfinate) which is then blended with vacuum gas oil (VGO) at valve X. The blended material is used as the whole feed to a Fluidized Catalytic Cracking Unit (FCCU). The present invention can be used to determine component lump information on any of all of four streams, the VGO (A1), the Resid (A2), the Residfinate (A3), and/or the whole feed (A4). The component lump information can be used for feedforward control of the hydrotreating unit (A2), for feedback control of the hydrotreating unit (A3), for feedforward control of the blending (A1 and A3), for feedback control of the blending (A4), and for feedforward control of the FCCU (A4).

On-line availability of lumps analyses can allow for real-time control of integrated refinery operations of blending and control of multiple units. FIG. 9 shows a refinery operation in which vacuum residue material (Resid in the Figure) is processed in a hydrogen treatment unit (labeled HT) to produce hydrotreated vacuum resid (Residfinate). The Residfinate material is then combined in varying proportions with Vacuum Gas Oil (VGO), and the ,blended material is used as the whole feed to a Fluidized Catalytic Cracking Unit (FCUU). Rapid online infrared analyses of the Residfinate and VGO streams permits continuous optimization of process operations. Control of the integrated process is obtained through adjustments of Hydrotreating severity, Residfinate/VGO mixing ratio, and FCCU process variables such as temperature.

Example 5:
Control of feed to a Catalytic Cracking Process

Figure 10:
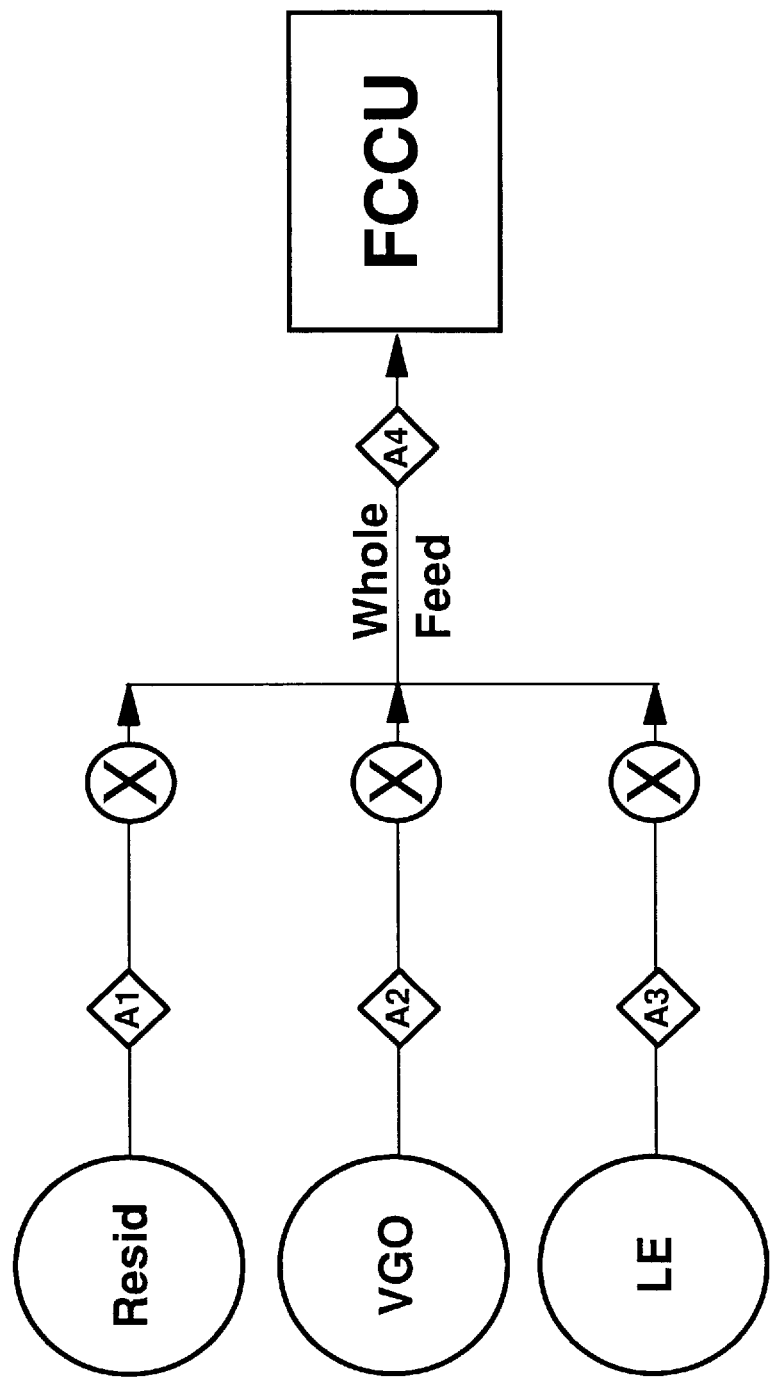
FIG. 10 shows a diagram of a refinery operation discussed in example 5. Vacuum residue (Resid), vacuum gas oil (VGO) and lube extract (LE) are held in three tanks. Component lump analyses A1, A2 and A3 are used for feedforward control the blending of whole feed from the three feed streams through adjustment of valves (X). Component lump analysis of the whole feed (A4) is used for feedback control of the blending, and/or feedforward control of the FCCU.

The online lumps analyses of individual component streams which are blended to produce a whole feed to a Catalytic Cracking Unit allows for feedforward control of the composition of the whole feed, within limits imposed by the compositions of the individual streams. FIG. 10 shows an example of a refinery wherein Catalytic Cracking feed components are segregated by type: Vacuum Gas Oil (VGO), Vacuum Resid (Resid) and Lube extract (LE) are held in three separate tanks. An online infrared analysis of the lump composition of each of the three component streams is performed. The compositional information provided by the analyzer is then used to control the mixing ratio of the three streams to provide control of two independent feed properties, for example, coke make and crackability. The feed analysis information is also used for control of FCCU process variables such as temperature.

What is claimed is:

1. A method to determine the concentration of compositional lumps in one or more boiling fractions selected from the group consisting of naphtha, distillate, vacuum gas oil, and vacuum residue, in a feed to or product from a hydrocarbon conversion process, hydrocarbon separation process and/or hydrocarbon blending process comprising:

(A) measuring the IR spectrum of said feed or product,
(B) applying a multivariate correlation to the spectrum to determine the concentration of
  (a) naphtha boiling range fraction lumps consisting of paraffins, cyclic olefins, noncyclic olefins, 1-ring naphthenes, 2-ring naphthenes, 1-ring alkyl aromatics, and 1-ring naphthenoaromatics, and/or (b) distillate boiling fraction lumps consisting of paraffins, 1-ring naphthenes, 2-ring naphthenes, 1-ring alkyl aromatics, 1-ring naphthenoarornatics, 2-ring alkyl aromatics, 2-ring naphthenoaromatics, and 2-ring denuded aromatics, and/or (c) one or more of vacuum gas oil and/or vacuum residue fraction lumps selected from the group consisting of
  (i) paraffins, 1-ring naphthenes, 2-ring naphthenes, 1-ring alkyl aromatics, 1-ring naphthenoaromatics, 2-ring alkyl aromatics, 2-ring naphthenoaromatics, 3-ring alkyl aromatics, 3-ring naphthenoaromatics, 3-ring denuded aromatics, 4+ring alkyl aromatics, 4-ring naphthenoaromatics, and 4+ring denuded aromatics;
  (ii) saturates, total 1-ring aromatics, total 2-ring aromatics, total 3-ring aromatics, total 4 ring aromatics and total polars;
  (iii) saturates, total 1-ring aromatics, 1-ring aromatic cores, total 2-ring aromatics, 2-ring aromatic cores, total 3-ring aromatics, 3-ring aromatic cores, total 4+ring aromatics, 4+ring aromatic cores, total polars, and polar aromatic cores, and combination thereof.

2. The method in claim 1 wherein said multivariate correlation is obtained by Multiple Linear Regression, Principal Components Regression, Partial Least Squares Regression, or Constrained Principal Spectra Analysis.

3. The method of claim 1 further comprising the step of determining elemental composition density, Micro Conradson Carbon, or Yield from distillation process.

4. The method of claim 3 wherein said elemental compositions include nitrogen or sulfur composition.

5. The method of claim 1 wherein said hydrocarbon conversion process is fluidized catalytic cracking.

6. The method of claim 1 wherein said hydrocarbon conversion process is hydrotreating.

7. The method of claim 1 further comprising the step of controlling said hydrocarbon conversion, separation or blending process.

8. The process of claim 1 wherein said compositional lumps are naphtha boiling range fraction lumps.

9. The process of claim 1 wherein said compositional lumps are distillate boiling fraction lumps.

10. The process of claim 1 wherein said compositional lumps are vacuum gas oil lumps.

11. The process of claim 1 wherein said compositional lumps are vacuum residue fraction lumps.

* * * * *